United States Patent [19]
Norman

[11] Patent Number: 6,042,585
[45] Date of Patent: Mar. 28, 2000

[54] SURGICAL WIRE DRIVER WITH ONE-HANDED GRIPPING ATTACHMENT

[75] Inventor: Gerould W. Norman, Clearwater, Fla.

[73] Assignee: Linvatec Corporation, Largo, Fla.

[21] Appl. No.: 09/243,051

[22] Filed: Feb. 2, 1999

Related U.S. Application Data

[62] Division of application No. 08/848,781, May 1, 1997, Pat. No. 5,902,306.

[51] Int. Cl.[7] ................................................. A61B 17/56
[52] U.S. Cl. ............................. 606/104; 606/103; 433/3
[58] Field of Search ........................... 606/74, 103, 104; 140/93 R; 433/3

[56] References Cited

U.S. PATENT DOCUMENTS

| | | |
|---|---|---|
| 2,682,063 | 6/1954 | Miloche ........................................ 433/3 |
| 3,071,861 | 1/1963 | Saffir . |
| 3,596,357 | 8/1971 | Matsumoto ................................. 433/3 |
| 4,736,742 | 4/1988 | Alexson et al. . |

*Primary Examiner*—Michael Buiz
*Assistant Examiner*—Julian W. Woo
*Attorney, Agent, or Firm*—Gene Warzecha

[57] ABSTRACT

A wire driver collet mechanism for selectively enabling the repositioning of a wire within a wire driver. The adjustable collet mechanism enables the wire to be repositioned under its own weight so that a user is not required to grasp the wire, thereby enabling one-handed operation of the wire driver. A method of adjusting a wire within a wire driver utilizes the steps of positioning the tip of a wire against a surface and allowing the wire to move under its own weight while moving the wire driver to position the wire as desired. The release of the wire is under the control of the hand holding the wire driver.

2 Claims, 4 Drawing Sheets

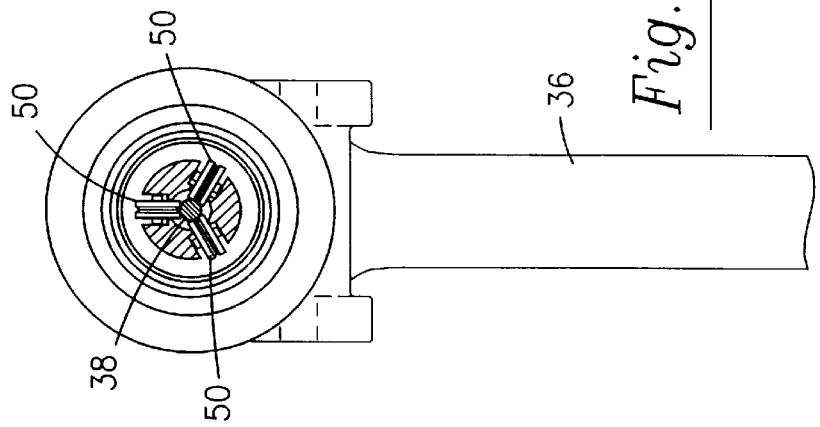
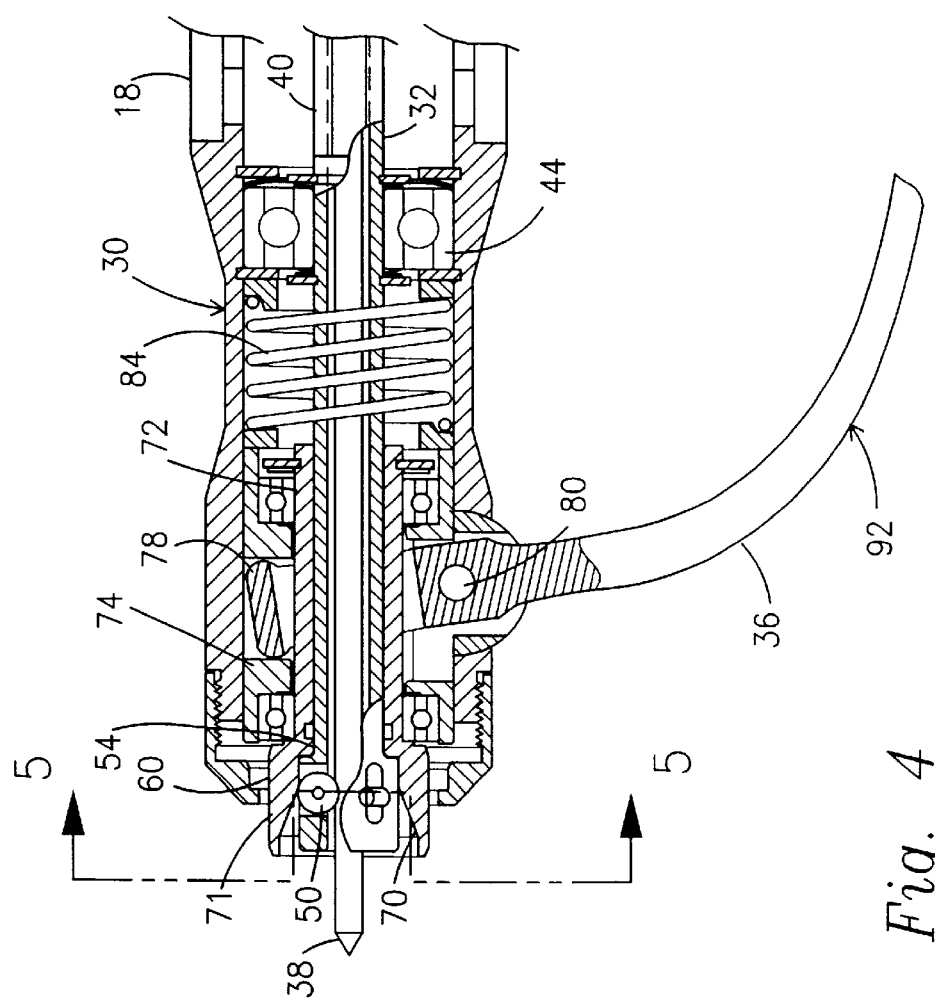
Fig. 5
Fig. 4

SURGICAL WIRE DRIVER WITH ONE-HANDED GRIPPING ATTACHMENT

This application is a division of Ser. No. 08/848,781 filed May 1, 1997 now U.S. Pat. No. 5,902,306.

BACKGROUND OF THE INVENTION

1. Field of the Invention

The invention relates to a surgical instrument for driving elongated pins or wires. In particular, the invention relates to a pin or wire driver having a collet mechanism which permits the pin or wire to be selectively released and engaged in order to be repositioned. The mechanism also permits automatic sizing of the collet to accept a range of pin/wire diameters. More particularly, the invention relates to a pin or wire driver collet adjustment mechanism suitable for one-handed operation.

2. Description of the Prior Art

Powered surgical instruments for driving elongated pins or wires are well known. While pins usually have larger diameters than wires, for purposes of this description, the terms "pins" and "wires" will be considered interchangeable. For simplicity, the term wire driver will be used to mean a driver for driving pins as well as wires or other similar, wire-like elongated devices (i.e. relatively rigid shafts which may or may not have pointed or drill tips and are usually, but not necessarily, made of metal such as stainless steel, nitinol, etc.) . Such instruments generally comprise a handpiece adapted to drive a cannulated drive shaft through which a wire may be passed. Since the wire to be driven may be relatively long, the drive shaft extends entirely through the handpiece from a proximal end to a distal end and is provided with a collet/chuck mechanism in order to selectively secure the wire to the drive shaft. The instrument is used to turn the drive shaft which, consequently, turns the wire in order to advance the wire extending from the distal end of the drive shaft into a bone or other structure at a surgical work site. Depending upon the desired penetration depth and other factors, the length of wire extending from the distal end of the drive shaft may need to be adjusted in order to optimize control of the wire. The wire's extended length is usually relatively short as the wire is first driven into the surgical work site and then, if additional penetration is desired, the grip on the wire is somehow overcome or released so the wire may be repositioned within the drive shaft and driven further into the surgical work site. Often, the collet mechanism is similar to a one-way clutch which permits the wire to be pulled out of the handpiece distally, but does not permit it to be pushed proximally. It will be noted that once the wire is sufficiently embedded at the surgical work site in a bone, for example, the distal end of the wire will be held in place by the bone. That is, in such a case there is no need for a surgeon to grasp the wire because the collet mechanism allows the wire to "slip" when the handpiece moves proximally along the wire (and the wire moves distally). The surgeon simply needs to move the handpiece relative to the wire until the desired length of wire extends from the drive shaft.

Some prior art wire drivers are provided with collet mechanisms which frictionally engage the wire at all times to a certain degree. This is necessary as a practical matter so that the wire does not simply fall out of the wire driver as the latter is manipulated during use. Other prior art wire drivers enable the wire to slide more freely. One example of such a prior art wire driver is described in U.S. Pat. No. 4,736,742 (Alexson et al.) which shows a wire driver attachment releasably attached to a gas operated handpiece having a pair of parallel output drive shafts, one of which is cannulated. The handpiece has a pistol-grip and a trigger for activating its drive shafts. The wire driver attachment fits on the handpiece in such a way as to align the cannulated output shaft with the wire being driven. A pivotable, spring-loaded lever is situated on the wire driver attachment and is movable between a release position, spaced away from the pistol-grip handle, and an engage position adjacent the handle. The action of the lever controls a cam surface in the attachment by moving it to selectively release or engage a plurality of locking balls circumferentially arranged around the wire being driven. The locking balls and associated cam surfaces are components of a threaded, cylindrical chuck which is adjustable by a user, using a second hand, so the wire can be frictionally held by the locking balls. However, this adjustment is usually made in practice just to size the collet for the wire. That is, in actual use the locking balls are adjusted close to but not simultaneously contacting the wire and cam surface. The wire may then be normally fully released so that it could fall out of the driver or the mechanism may be adjusted so the wire can be slid longitudinally through the chuck with the lever in the release position (i.e. its normally biased position). In either case, the wire would be tightly engaged by the locking balls when the lever is in the engage position. The handpiece is activated by a user pulling an activating trigger while moving the lever to the engage position. When pressure is removed from the lever, it returns to its release (i.e. lightly gripping or sliding) position in which the device allows longitudinal movement of the wire relative to the chuck. In any case, the wire driver shown in this patent requires a two-handed operation for any adjustment of the cylindrical part which sizes the mechanism to match the wire then in use.

Another known wire driver assembly utilizes a collet mechanism based on a plurality of gripper discs circumferentially arranged about a wire to be driven. Such a device is available from Zimmer, Inc., Warsaw, Ind. (an affiliate of the assignee of this invention) in the form of a lever-less pin driver assembly more particularly described below by reference to FIG. 6.

The aforementioned devices as well as other conventional wire drivers are designed and adjusted to hold wires in position so they will not move or fall out of the collet under their own weight. As mentioned, this is necessary as a practical matter to prevent the wires from falling out of the handpiece. However, this produces a disadvantage in that once the wire has been initially inserted into the driver, minor adjustments of the wire position in the collet are not easily achievable. The surgeon must either use his/her other hand or the assistance of another person in order to achieve the precise wire position desired. Since the surgeon's other hand may already be occupied, this is an obvious limitation which may adversely affect the efficiency of the surgical procedure.

It has been found that it would be desirable to enable a surgeon to simply rest the distal tip of the wire against a sterile surface (such as a surgical drape, etc.) and, with the hand holding the driver, release the wire so it can fall under its own weight. This would enable the surgeon to move the driver up or down the wire without the assistance of another person and without having to grasp the wire, while also having the driver normally maintain a light grip on the wire preventing it from falling out. The same mechanism enables the wire driver to automatically adjust its collet size to accept a wide range of wire diameters.

Accordingly, it is an object of this invention to produce a wire driver collet mechanism which enables the wire to be selectively repositioned or engaged.

It is a further object of this invention to produce a wire driver collet mechanism which enables the wire to be selectively repositioned under its own weight.

It is another object of this invention to produce a wire driver collet mechanism, for a wire driver handpiece, in which the wire may be selectively repositioned easily with a one-handed operation utilizing the same hand which holds the wire driver handpiece. That is, it is also an object of this invention to produce a wire driver which enables a user to selectively reposition the wire driver on the wire while using only one hand to hold the driver and control the collet holding the wire.

It is another object of this invention to enable this to be done with a lever-operated wire driver attachment since that is a structure commonly used in similar devices.

It is an additional object of this invention to produce a wire driver collet mechanism which automatically adjusts to accept a wide range of wire diameters.

SUMMARY OF THE INVENTION

These and other objects of this invention are achieved by the preferred embodiment disclosed herein which is a surgical instrument comprising a handpiece and a wire driver attachment for receiving and driving a wire-like member. The handpiece has a handle for being held by a hand and the wire driver attachment has a gripper means for selectively securing the wire-like member to a drive shaft in the handpiece. The gripper means is movable between a release position in which the wire-like member is movable under its own weight, and an engage position in which the wire-like member is frictionally retained sufficiently to be driven. An adjustment means is connected to the gripper means for selectively moving it between the enable and the release positions, the adjustment means being operable by the hand holding the handpiece. Once the wire is loaded into the driver, all further desired adjustments of exposed wire lengths are accomplished with the same hand which holds the handpiece. In the preferred embodiment the adjustment is done by a lever actuator situated in front of a pistol-grip handle, the lever being pivotable relative to the handle so it can be moved by the fingers of the hand holding the handpiece.

The invention also resides in the method of adjusting a wire-like member within a wire driver such as that described above. The method comprises the steps of providing a surgical wire driver, holding it in one hand, and placing a surgical wire within the cannulated drive shaft. The method further comprises the steps of providing a collet means for securing the wire to the drive shaft and providing an actuating member for selectively moving the collet means between a release and engage position. The actuating member is moved to the release position by a portion of the same hand in which the wire driver is held thus allowing the wire to move by its own weight relative to the driver until it reaches a selected position. The actuating member is then released so that it returns to its normally biased engage position.

BRIEF DESCRIPTION OF THE DRAWINGS

FIG. 4 is a view of FIG. 2 showing the wire driver attachment in an engage position.

FIG. 5 is a sectional view of FIG. 4 taken along the line 5—5.

DESCRIPTION OF THE PREFERRED EMBODIMENT

Figure 1:
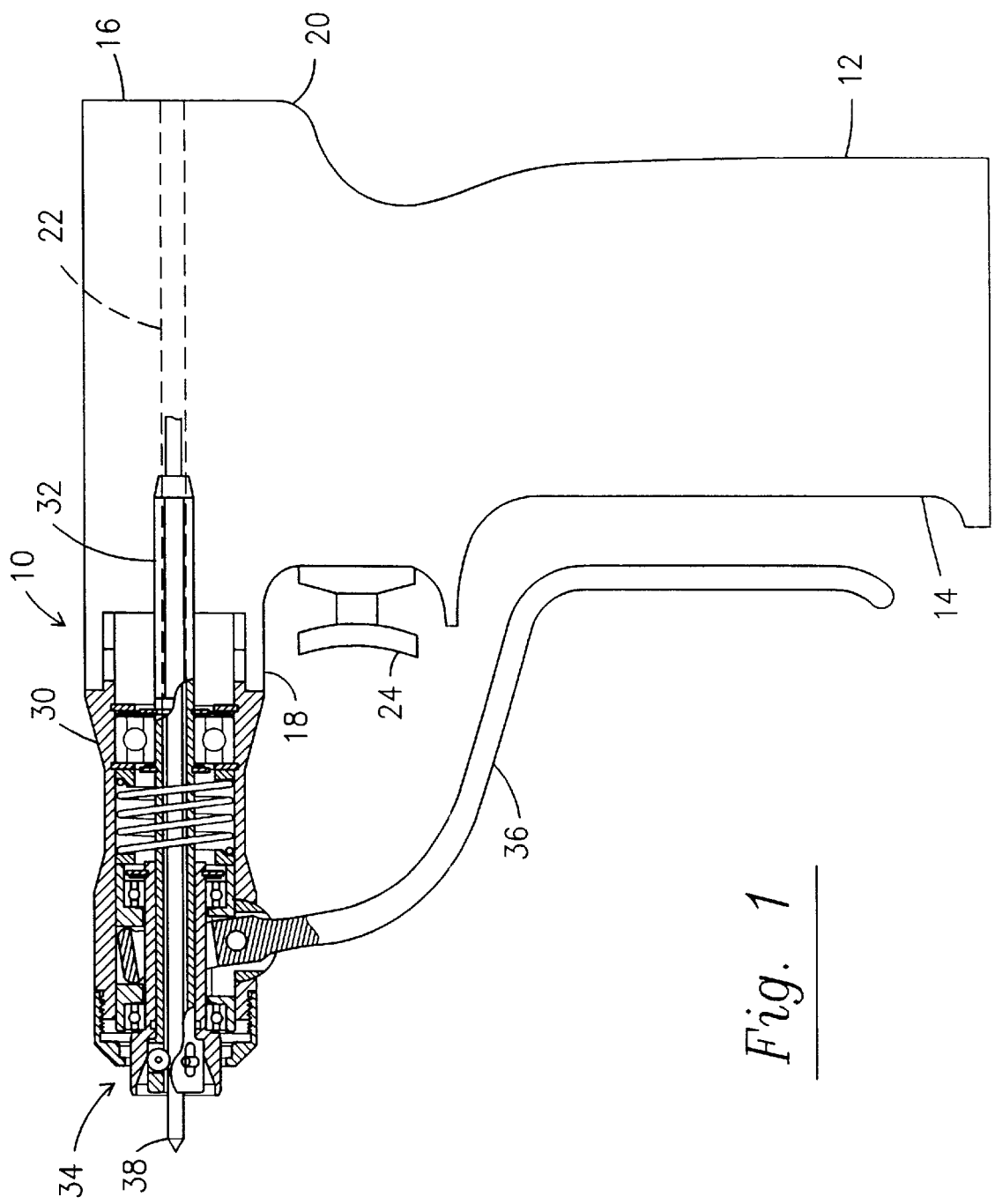
FIG. 1 is a side elevational schematic view partly in cross-section of a wire driver constructed in accordance with the principles of this invention.

As shown in FIG. 1, wire driver 10 comprises a handpiece 12 having a pistol-grip handle 14 and a top, transverse body portion 16. Body portion 16 has a distal end 18 and a proximal end 20 and it and handpiece 12 contain a conventional motor and cannulated drive shaft (not shown) for driving a wire inserted through bore 22 extending entirely through body portion 16 from proximal end 18 to distal end 20. The handpiece is also provided with a trigger 24 for activating the drive mechanism which may be either pneumatic or electric and forms no part of this invention.

Wire driver attachment 30 is secured, preferably releasably, (by means not shown) to distal end 18 of the top body portion 16 so as to engage its rotatable cannulated drive shaft 32 with the motor drive shaft (not shown) in handpiece 10. Attachment 30 comprises a collet mechanism 34 which selectively engages and releases wire 38 via a pivotable control lever 36, the operation of which will be best understood by reference to FIGS. 2 through 5. Drive shaft 32 has a hexagonally profiled outer surface at its proximal end 40 for engagement within a complementarily shaped motor drive shaft (not shown) and a cylindrical outer surface at its distal end 42 rotatably situated within bearings 44, 46 and 48. Collet mechanism 34 circumferentially surrounds wire 38 at the distal end of the wire driver attachment and comprises a plurality of circumferentially arranged gripper discs 50 retained within a gripper housing 52 at the distal end 54 of drive shaft 32. As will be understood below, all of the gripper discs operate in conjunction with a cylindrical cam assembly 60 which is longitudinally positioned to either place the gripper discs in an engage position or allow them to move into a release position.

Figure 3:
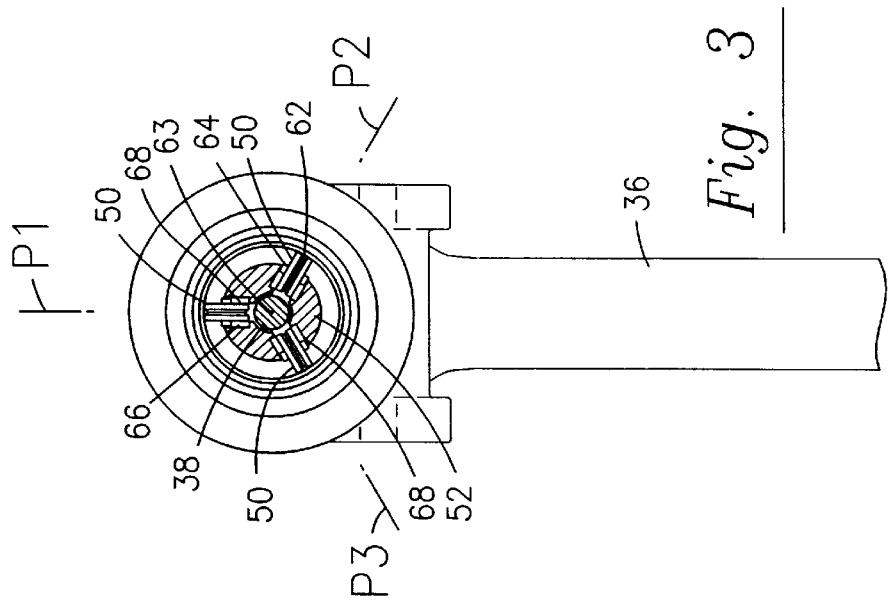
FIG. 3 is a sectional view of FIG. 2 taken along the line 3—3.

Gripper discs such as those shown are conventional structures which are not themselves part of the invention. Nevertheless, some brief description of the operation of the gripper discs is helpful to understand the invention. In the preferred embodiment, three gripper discs 50 are positioned equiangularly about the axis 63 so that the planar bodies of the discs are rotatable within circumferentially spaced axial planes P1, P2 and P3, as best seen in FIG. 3. Each gripper disc 50 has an annular groove 62 designed to enhance the frictional engagement between the disc and an associated wire 38 which is to be gripped. Each disc is situated in a radial slot 68 formed in the exterior cylindrical surface of housing 52 at the distal end of drive shaft 32 and each slot has a transverse width sufficient to accommodate the cylindrical body of its associated disc. Each slot 68 is further provided with a pair of opposed slots 66 for receiving the ends of disc axle members 64 thereby enabling each gripper disc to rotate about its axis and to slide under its own weight radially inwardly and outwardly along this axis slot.

Figure 6:
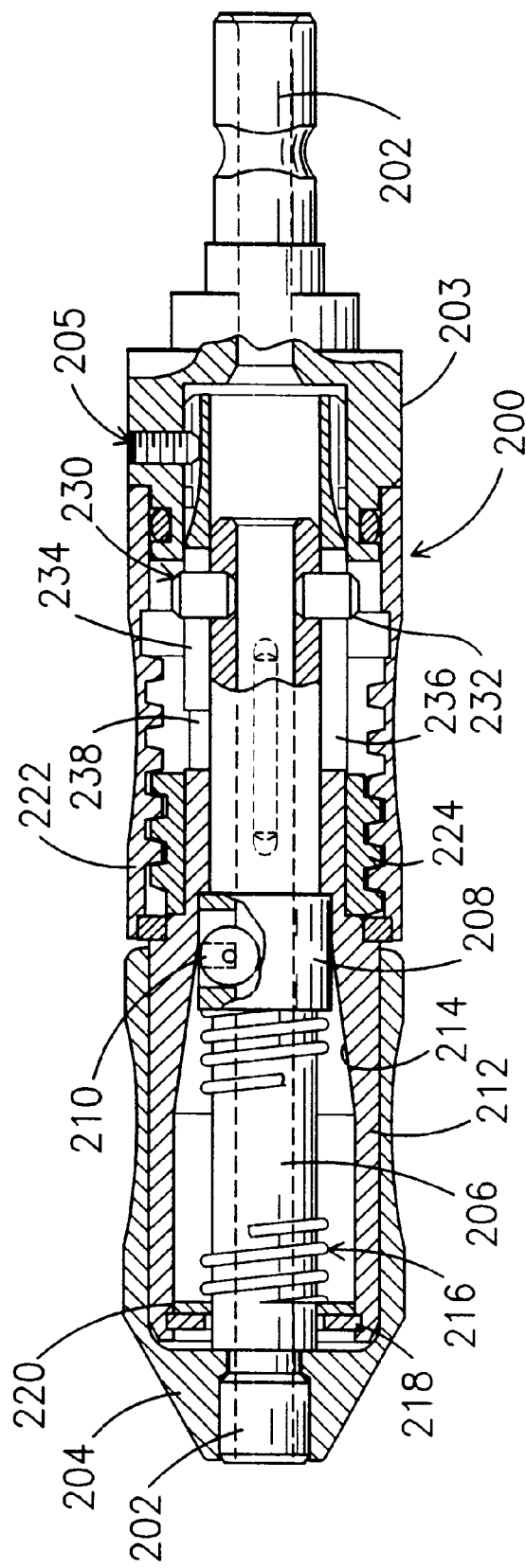
FIG. 6 is a view of a prior art pin driver assembly showing the use of the gripper discs used in the present invention.

As shown in FIG. 6, gripper discs such as those described herein have been used in prior art wire driver assemblies although their use is considerably enhanced by the subject invention. A prior art wire driver assembly 200, in the form of an attachment for being secured to a handpiece similar to handpiece 10, comprises a throughbore 202 for receiving a wire to be driven. The assembly 200 is secured to an adapter 203 which may be one of several configurations adapted in order to fit the assembly to a particular handpiece (not shown). The adapter is threaded into the body of assembly 200 and secured by a set screw 205. A nose member 204 is secured to the distal end of a cannulated drive shaft 206 which carries at its mid-section a gripper housing 208 having a plurality of circumferentially arranged gripper discs 210 (only one of which is shown). A cylindrical cam assembly 212 is interposed between nose member 204 and drive shaft 206 so as to provide a conically tapered cam surface 214 adjacent the gripper discs. Spring 216 is retained between ring 218/washer 220 at its distal end and gripper housing 208 at its proximal end. The spring biases drive shaft 206 and gripper discs 210 proximally, thus urging the discs against cam surface 214 (the gripper discs would otherwise be loosely movable radially inwardly and outwardly as described above). Cylindrical cam assembly 212 is movable against the force of spring 216 between an engage position, as shown in FIG. 6, and a release position (not shown) in which gripper housing 208 is displaced to the left of the position shown in FIG. 6—out of engagement with cam surface 214. Such longitudinal movement of the cam assembly is controlled by nose member 204 and adjustment ring 222 threadably engaged with locking sleeve 224 concentrically situated about the proximal end of cylindrical cam assembly 212. Drive shaft 206 is restricted to be only longitudinally movable relative to cylindrical cam assembly 212 by a conventional pin and slot arrangement: diametrically opposed pins 230, 232 are attached to the drive shaft and received within a corresponding pair of longitudinal slots 234, 236, respectively, extending through the surface of cam assembly 212 to prevent relative rotation. A pair of transverse slots 238 (only one of which is shown) at the distal end of the longitudinal slots enables the nose member and drive shaft to be turned into an open and locked position to keep tension off the gripper discs to enable loading of a wire. Locking sleeve 224 is threadably adjustable between the position shown in FIG. 6, in which the sleeve abuts a proximally facing shoulder on the cam assembly and thereby permits the attachment to be placed into an open/load configuration in which the pins 230, 232 engage slots 238 to keep the device open to enable wire loading, and a locked position (not shown) in which the sleeve is spaced proximally from the shoulder as adjustment ring 222 is turned. The position of sleeve 224 is continuously variable between these two extremes and it is only at the locked position that the sleeve abuts pins 230, 232 and prevents any motion of the drive shaft relative to the cam assembly. In all but the open/load and locked positions a wire inserted through bore 202 will be gripped solely by spring tension urging housing 208 in a proximal direction against cam surface 214. By virtue of the relatively small angle of inclination of conical cam surface 214, the wire being driven will be tightly gripped as it is pushed distally into a bone and then, once sufficiently embedded into the bone to be tightly held by the bone, the wire driver may be pulled back, enabling the wire to roll along the gripper discs to a new position. In the open/load position the spring will be effectively disengaged from the discs and they will be free to move under their own weight, and in the locked position the threaded sleeve 224 will urge the cam surface 214 against the discs and add to the spring force, thus effectively limiting the ability of the discs to roll along the wire.

Figure 2:
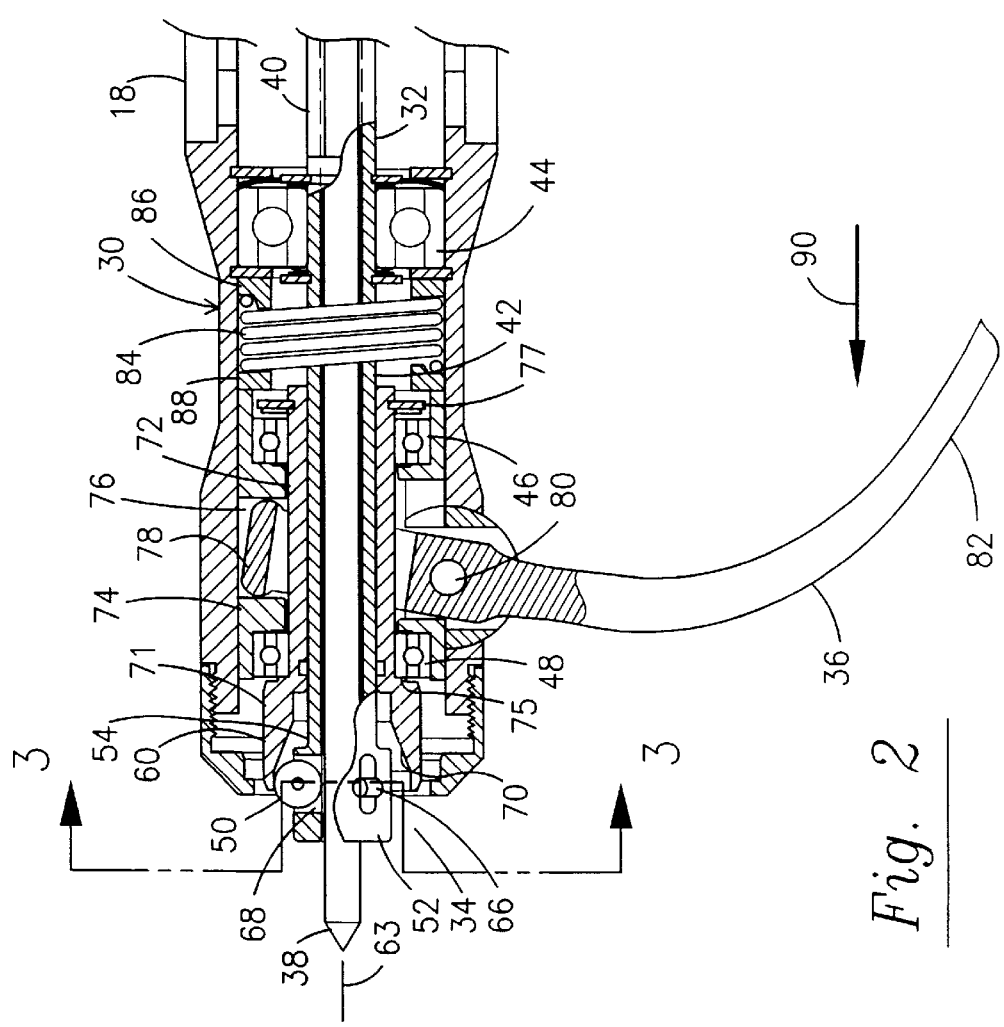
FIG. 2 shows the wire driver attachment of FIG. 1 in the release position.

Returning now to FIG. 2, cylindrical cam assembly 60 comprises a conical cam surface 70 at the distal end of a cam body 71, a tubular body 72 interposed between the cylindrical drive shaft portion 42 and bearings 46 and 48, and a slidable, cylindrical block assembly 74 which actually receives bearings 46 and 48 at its opposing ends. Block assembly 74 is rotatably secured to cam assembly 60 by being retained between shoulder 75 on the exterior surface of the cam body 71 and a retaining ring 77. Block assembly 74 is provided with a central transverse aperture 76 surrounding tubular body 72 and within which is situated the proximal end 78 of lever 36. The lever is pivotably attached at pivot point 80 to the housing of wire driver attachment 30 so that movement of the distal portion 82 of lever 36 about pivot 80 will cause the proximal end 78 to move block assembly 74. Spring 84 is provided between bushings or end caps 86 and 88 and biases block assembly 74 in the distal direction. Thus, the position of the components shown in FIG. 4 represents the normal, i.e. engage position of the device in which the spring tension ultimately acts on gripper discs 50 to engage a wire. This spring tension also causes lever 36 to be pivoted counterclockwise about pivot 80. As shown in FIG. 2, lever 36 may be pushed in a direction 90 by a user. Such distal motion of lever 36—which may be done by the fingers of the same hand gripping handle 14—causes cam assembly 60 to move proximally against the spring tension into an open/load position, thereby allowing gripper discs 50 to be released from their engagement with the radially inner portion of cam surface 70. This is diagrammatically shown in FIG. 3 by representing the gripper discs as being at their radially outermost position, however, it will be understood that the gripper discs are not spring loaded so as to automatically cause all of them to move radially outwardly in all directions simultaneously. They will, nevertheless, individually move radially outwardly under the influence of gravity if the wire driver happens to be oriented to enable this. In any event, the frictional engagement between cam surface 70 and those discs that do not fall away will be reduced to such a level that the wire 38 may fall under its own weight through bore 22 in either the proximal or distal direction, assuming of course that the driver is held so as to orient the wire vertically.

Once the wire is positioned as desired, one simply needs to remove the outwardly directed force on the lever as shown in FIG. 4. This will enable the spring to return to its normally "closed" position in which the gripper discs move into engagement with the wire. In this position the wire is automatically gripped to keep it from falling out. An additional force 92 may then be exerted on lever 36 if the user simply grips lever 36 simultaneously with handle 14. This extra force enhances the grip on the wire by causing the upper end 78 of lever 36 to urge cam assembly 60 distally thereby bringing gripper discs 50 into progressively tighter engagement with cam surface 70 until the gripper discs tightly engage wire 38.

Spring 84 will ensure that the cam surface 70 is urged distally with sufficient force to properly grip the wire sizes for which the particular attachment is designed. While in the preferred embodiment the acceptable wire sizes range from 0.079 inches (2 mm) in diameter as shown in FIGS. 4 and 5 to 0.126 inches (3.2 mm) in diameter as shown in FIGS. 2 and 3, it will be understood that the invention is adaptable to all wire diameters by simply making dimensional changes accordingly.

While the preferred embodiment is described with gripper discs 50, it will be understood that locking balls or other rolling elements could also be adapted for use instead of the discs. In each case, the operation of the device between a normally closed (locked) position and an open/load position is under the control of the hand holding the wire driver and no further adjustment is necessary, regardless of wire size.

Similarly, while shown as a lever actuated, pistol-grip type of handpiece, the principles of this invention may be adapted to a variety of other configurations such as, for example, to a pencil-grip type of handpiece utilizing a slide actuated mechanism instead of a lever.

It will be understood by those skilled in the art that numerous improvements and modifications may be made to the preferred embodiment of the invention disclosed herein without departing from the spirit and scope thereof.

What is claimed is:

1. A method for manually adjusting the length of a surgical wire-like member extending from a surgical wire driver held by a user in one hand, comprising the steps of:

providing a surgical wire driver having a cannulated drive shaft for receiving a surgical wire-like member;

holding the surgical wire driver in one hand;

placing a surgical wire-like member within the cannulated drive shaft of the surgical wire driver;

providing a collet means for securing the wire-like member to the cannulated drive shaft, said collet means movable between an engage position and a release position;

providing an actuating member for selectively moving said collet means between said release and engage position;

moving the actuating member, by a portion of the same hand in which the wire driver is held, to the release position;

permitting the wire-like member to move by its own weight relative to the driver until it reaches a selected position;

moving the actuating member to place said collet means in said engage position.

2. A method according to claim 1 wherein the step of permitting the wire to move further comprises:

moving the wire driver to orient the wire-like member vertically;

placing the distal tip of the wire-like member against a surface; and moving the wire driver along the wire-like member until a desired relative position of the wire driver and wire is attained.

* * * * *